(12) United States Patent
Sikora et al.

(10) Patent No.: US 7,465,308 B2
(45) Date of Patent: Dec. 16, 2008

(54) FIXATION DEVICE

(75) Inventors: George Sikora, Bridgewater, MA (US); Aaron Hecker, West Roxbury, MA (US); Charles H. Brown, Jr., Wellesley, MA (US)

(73) Assignee: Smith & Nephew, Inc., Memphis, TN (US)

( * ) Notice: Subject to any disclaimer, the term of this patent is extended or adjusted under 35 U.S.C. 154(b) by 415 days.

(21) Appl. No.: 10/410,868

(22) Filed: Apr. 10, 2003

(65) Prior Publication Data

US 2004/0204722 A1   Oct. 14, 2004

(51) Int. Cl.
   *A61B 17/08* (2006.01)
   *A61B 17/06* (2006.01)
(52) U.S. Cl. .................................................. 606/151
(58) Field of Classification Search ............. 606/232, 606/233, 224, 225, 205–209, 148, 151, 144, 606/139, 222, 223
   See application file for complete search history.

(56) References Cited

U.S. PATENT DOCUMENTS

| | | | |
|---|---|---|---|
| 5,144,961 A | | 9/1992 | Chen et al. |
| 5,284,485 A | * | 2/1994 | Kammerer et al. ........... 606/148 |
| 5,500,000 A | | 3/1996 | Feagin et al. |
| 5,540,703 A | * | 7/1996 | Barker et al. ................ 606/139 |
| 5,623,293 A | * | 4/1997 | Aoki ............................ 347/56 |
| 5,628,756 A | * | 5/1997 | Barker et al. ................ 606/139 |
| 5,643,293 A | * | 7/1997 | Kogasaka et al. ........... 606/148 |
| 5,769,862 A | | 6/1998 | Kammerer et al. |
| 6,283,996 B1 | | 9/2001 | Chervitz et al. |
| 6,599,310 B2 | * | 7/2003 | Leung et al. ................ 606/228 |
| 6,652,561 B1 | | 11/2003 | Tran |
| 6,663,633 B1 | * | 12/2003 | Pierson, III .................. 606/72 |
| 7,048,754 B2 | * | 5/2006 | Martin et al. ................ 606/232 |
| 2002/0173788 A1 | | 11/2002 | Bojarski et al. |
| 2003/0050668 A1 | | 3/2003 | Lee |
| 2003/0055438 A1 | | 3/2003 | Hirata |
| 2003/0097082 A1 | * | 5/2003 | Purdy et al. .................. 600/594 |

OTHER PUBLICATIONS

Ashley Clifford W. "Das Ashley-Buch der Knoten" 1982, Maritim, Hamburg XP 002292309, p. 85 and p. 225 (2 pages).
International Search Report Form PCT/ISA/220 (9 pages).
Written Opinion of the International Searching Authority, Form PCT/ISA/237 (7 pages).
International Preliminary Examination Report for International Application No. PCT/US2004/010807, dated Jul. 5, 2005, 6 pages.

* cited by examiner

*Primary Examiner*—Pedro Philogene
(74) *Attorney, Agent, or Firm*—Fish & Richardson P.C.

(57) ABSTRACT

A medical device that attaches to tissue without requiring stitching includes a tissue fixation device having a first sub-loop and a second sub-loop, and an assisting member disposed through the first sub-loop and through the second sub-loop. The tissue fixation device includes an adjustable, flexible member formed by inserting one end portion of the flexible member through another end portion of the flexible member, and first and second sub-loops formed by crossing a portion of the flexible member over a different portion of the flexible member.

20 Claims, 7 Drawing Sheets

FIXATION DEVICE

TECHNICAL FIELD

This invention relates to medical devices, and more particularly to a fixation device.

BACKGROUND

To perform a surgical repair, e.g., of a torn anterior cruciate ligament ("ACL"), the surgeon typically connects a length of suture to the replacement ACL soft tissue graft. The suture enables the surgeon to pull the tissue graft through holes formed in the tibia and femur for receiving the tissue graft. Typically, the surgeon attaches the suture to the ACL soft tissue graft using a whipstitch. Stitching the suture to the tissue graft using a whipstitch usually takes over two minutes per tissue graft.

SUMMARY

This invention relates to a fixation device that attaches to a tissue graft without requiring stitching. One advantage is that the time it takes for the surgeon to attach the fixation device to the tissue graft is shorter than the time it takes to whipstitch a suture to the tissue graft. In one aspect, there is a tissue fixation device that includes a member having a first sub-loop and a second sub-loop, where each sub-loop is configured to receive a length of tissue therethrough. In one example, the member comprises suture. In another example, the member further includes a third sub-loop configured to receive a length of tissue therethrough.

In another aspect, there is a medical device including an adjustable loop and an assisting member. The adjustable member includes a first sub-loop and a second sub-loop configured to receive a length of tissue therethrough. The assisting member is disposed through the first sub-loop and through the second sub-loop. In one example, the assisting member comprises a medical grasping device. In another example, the assisting member comprises a cannula. In another example, the adjustable member is a first member. In this example, the medical device also includes a second adjustable member including a first sub-loop and a second sub-loop, wherein the assisting member is further disposed through the first sub-loop of the second adjustable tissue fixation device and through the second sub-loop of the second adjustable tissue fixation device. In another example, the adjustable member comprises suture. In yet another example, the adjustable member also includes a third sub-loop configured to receive a length of tissue therethrough.

In yet another aspect, there is a tissue fixation device including an adjustable, flexible member. The adjustable, flexible member is formed by inserting one end portion of the flexible member through another end portion of the flexible member. The adjustable member is further formed into a first sub-loop and a second sub-loop. Crossing a portion of the flexible member over a different portion of the flexible member forms the first sub-loop and the second sub-loop. The first sub-loop and the second sub-loop are configured to fixate onto tissue.

In one example, the flexible member comprises suture. In another example, the sub-loops are configured to fixate on ligament or tendon tissue. In another example, the adjustable member also includes a third sub-loop. In yet another example, the adjustable member is a first adjustable member. In this example, the fixation device further includes a second adjustable member including a first sub-loop and a second sub-loop.

In another aspect, there is a medical device that includes a plurality of adjustable suture members and a cannula. The plurality of adjustable suture members each include a first sub-loop, a second sub-loop, and a third sub-loop, where each sub-loop is configured to receive a length of tissue therethrough. The cannula is disposed through the sub-loops of each of the plurality of adjustable suture members.

In another aspect, there is a method for making a medical device. He method includes inserting one end portion of a flexible member through another end portion of the flexible member to form an adjustable loop. The method further includes locating a first portion of the adjustable loop over a second portion of the adjustable loop to form a first sub-loop and a second sub-loop, where the sub-loops configured to receive a length of tissue.

In one example, the method also includes locating a first portion of the second sub-loop over a second portion of the second sub-loop to form a third sub-loop. In another example, the flexible member comprises suture. In another example, the method also includes locating further comprises rotating a portion of the adjustable loop approximately 180 degrees of rotation. In another example, the method also includes sliding the first portion of the adjustable loop over the second portion of the adjustable loop to form a first sub-loop and a second sub-loop.

In yet another example, the method also includes locating a first portion of an assisting member within the first sub-loop and a second portion of the assisting member within the second sub-loop. In one example, the assisting member includes a medical grasping device. In another example, the assisting member comprises a cannula. In another example, the flexible member is a first flexible member. In this example, the method also includes inserting one end portion of a second flexible member through another end portion of the second flexible member to form a second adjustable loop, locating a first portion of the second adjustable loop over a second portion of the second adjustable loop to form a first sub-loop and a second sub-loop and locating a fourth portion of the assisting member within the first sub-loop of the second flexible member and a fifth portion of the assisting member within the second sub-loop of the second flexible member.

In another aspect, there is a method for attaching a fixation device to tissue. The method includes moving a first sub-loop and a second sub-loop of the fixation device over a portion of the tissue and pulling an end portion of the fixation device to reduce the size of the sub-loops to fixate the fixation device to the portion of the tissue. In one example, the method also includes moving a third sub-loop over the portion of tissue. In another example, the method also includes grasping tissue with an assisting member located within the first and second sub-loops. In another example, the method also includes sliding the first sub-loop and the second sub-loop off of the assisting member. In another example, the fixation device comprises suture. In another example, the tissue comprises ligament or tendon graft.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
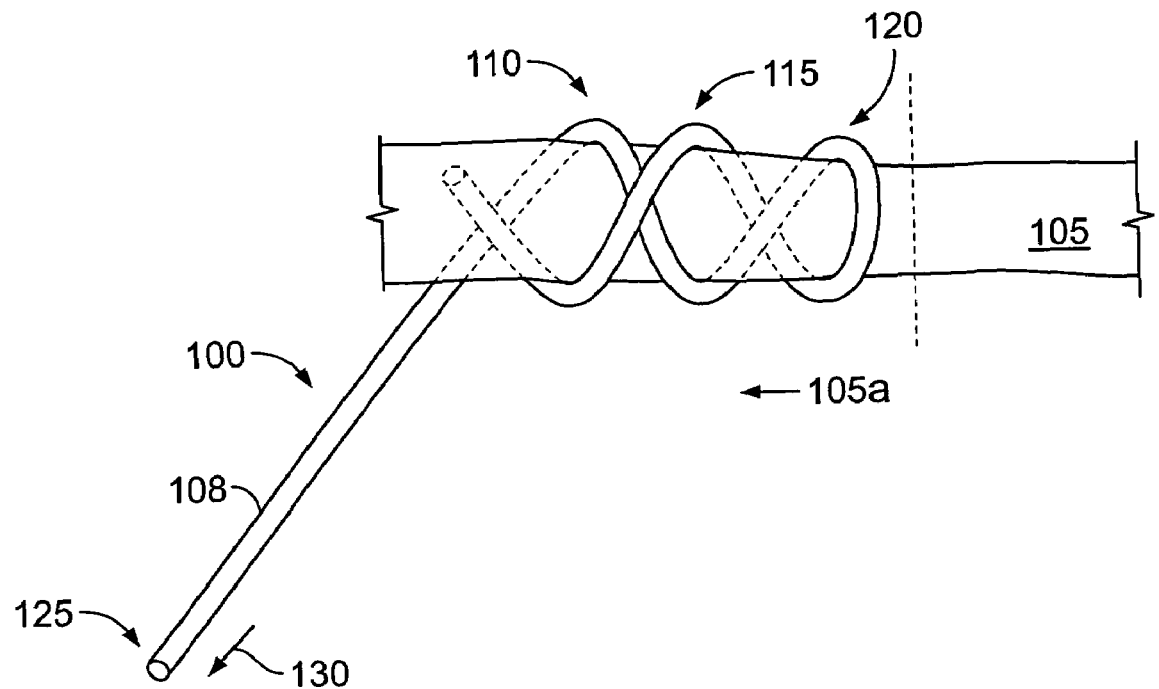
FIG. 1 is a side view of a fixation device connected to tissue.

Referring to FIG. 1, a fixation device 100 includes a length of flexible material, e.g., a suture 108 formed into a first sub-loop 110, a second sub-loop 115, and a third sub-loop 120. As described in more detail below, sub-loops 110, 115, and 120 are formed and wrapped around tissue 105 such that when a surgeon pulls an end 125 of suture 108 in a direction indicated by arrow 130, sub-loops 110, 115, and 120 constrict around and thus fixate on a portion 105a of tissue 105. This allows the surgeon to pull tissue 105 by pulling end 125 of fixation device 100 and provides a limitless gripping force in that as the tension applied to 125 increases, the constriction of the loops around tissue 105 increases. In other words, the harder the surgeon pulls, the tighter sub-loops 110, 115, and 120 constrict around portion 105a of tissue 105. Tissue 105 includes, for example, a replacement ligament or tendon. Suture 108 includes, for example, medical grade suture suitable for use in a surgical procedure.

Figure 2:
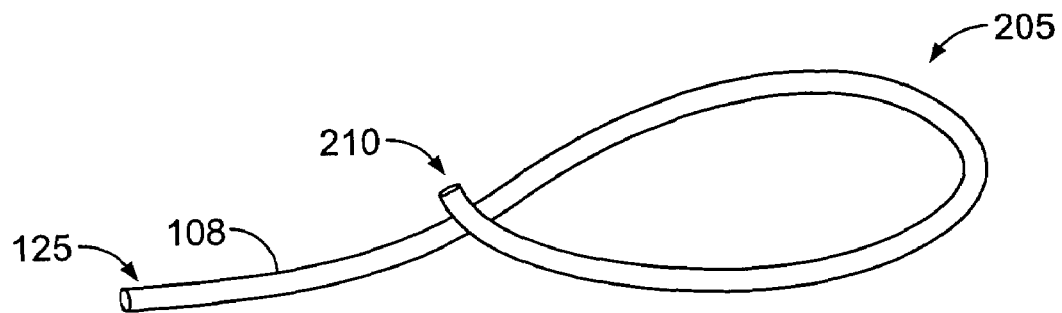
FIG. 2 is a side view of an adjustable loop.
Figure 3:
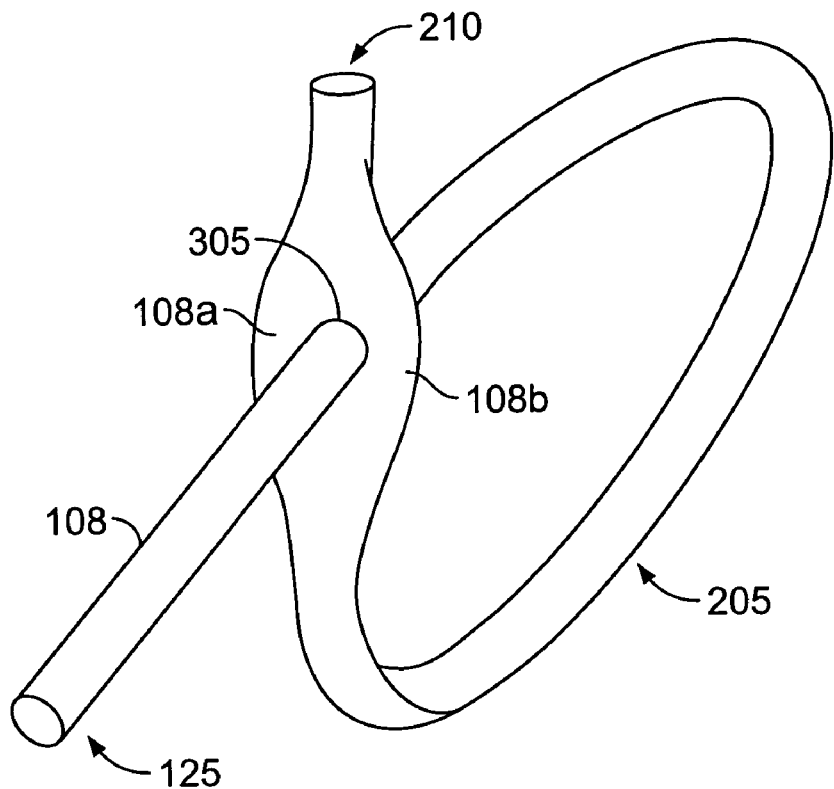
FIG. 3 is a perspective view of the adjustable loop.

Referring to FIGS. 2 and 3, fixation device 100 is constructed by initially forming suture 108 into an adjustable loop 205. Adjustable loop 205 is formed by passing end 125 of suture 108 through an opposite end 210 of suture 108. For example, suture end 125 is pushed through end 210 such that portions 108a and 108b of suture end 210 define a hole 305. Alternatively, hole 305 is preformed in suture end 210 and suture end 125 is passed through the hole. As constructed, suture 108 easily slides through hole 305 to increase or decrease the size of adjustable loop 205. This mechanism also allows the surgeon to increase and decrease the size of any sub-loops formed from adjustable loop 205 when the surgeon pulls on end 125.

Figure 4:
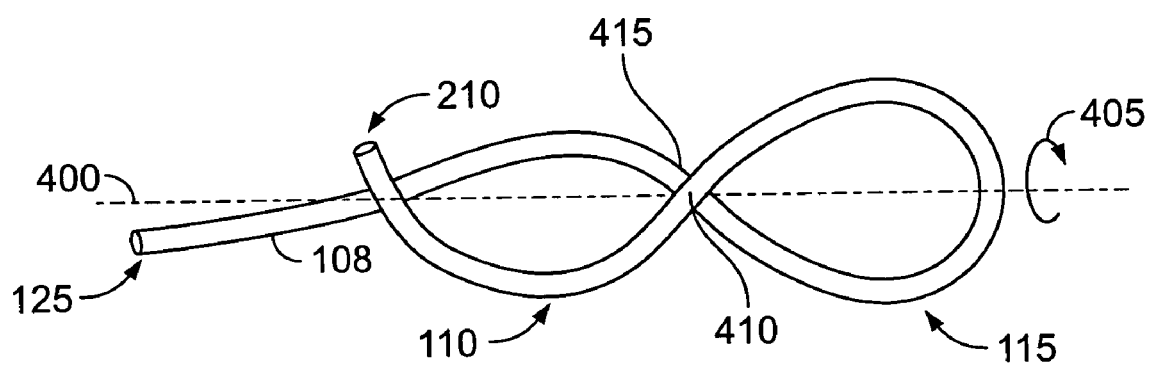
FIG. 4 is a side view of two sub-loops formed from the adjustable loop.

Referring to FIG. 4, rotating adjustable loop 205 one-half turn, approximately 180 degrees, around an axis 400 generates sub-loops 110 and 115. As illustrated, the rotation is in a direction indicated by arrow 405. This rotation causes a first portion 410 of adjustable loop 205 to cross and overlap a second portion 415 of adjustable loop 205. The overlapping portions 410 and 415 define part of the boundaries of sub-loops 110 and 115. Axis 400 also represents how tissue 105 (FIG. 1) passes through sub-loops 110 and 115. As illustrated, tissue 105 goes into the center of second sub-loop 115, under (with respect to the illustrated viewing angle) overlapping portions 410 and 415, and out of the center of the first sub-loop 110.

Figure 5:
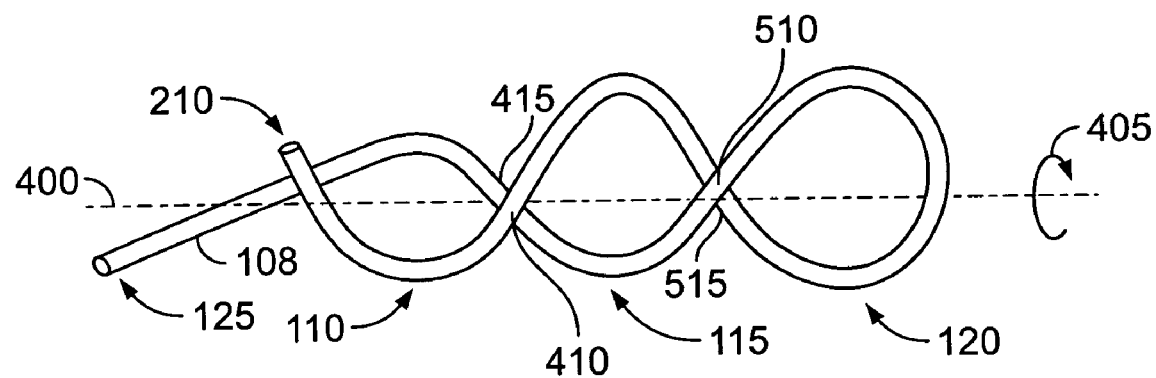
FIG. 5 is a side view of three sub-loops formed from the adjustable loop to produce the fixation device.

Referring to FIG. 5, rotating sub-loop 115 another one-half turn, approximately 180 degrees, around axis 400 generates the third sub-loop 120. This rotation causes a third portion 510 of adjustable loop 205 to cross and overlap a fourth portion 515 of adjustable loop 205. The overlapping portions 510 and 515 define part of the boundaries of sub-loops 115 and 120. Axis 400 also represents how tissue 105 (FIG. 1) passes through sub-loops 110, 115 and 120. As illustrated, tissue 105 goes into the center of third sub-loop 120 and over (with respect to the illustrated viewing angle) overlapping portions 510 and 515. Tissue 105 also goes into the center of second sub-loop 115, under (with respect to the illustrated viewing angle) overlapping portions 410 and 415, and out of the center of the first sub-loop 110. This process can be repeated multiple times to generate multiple sub-loops from adjustable loop 205. An advantage to having three sub-loops over two sub-loops, as depicted in FIG. 4, is that additional loops provide greater tissue to suture purchase, along with greater capacity for load distribution.

Figure 6:
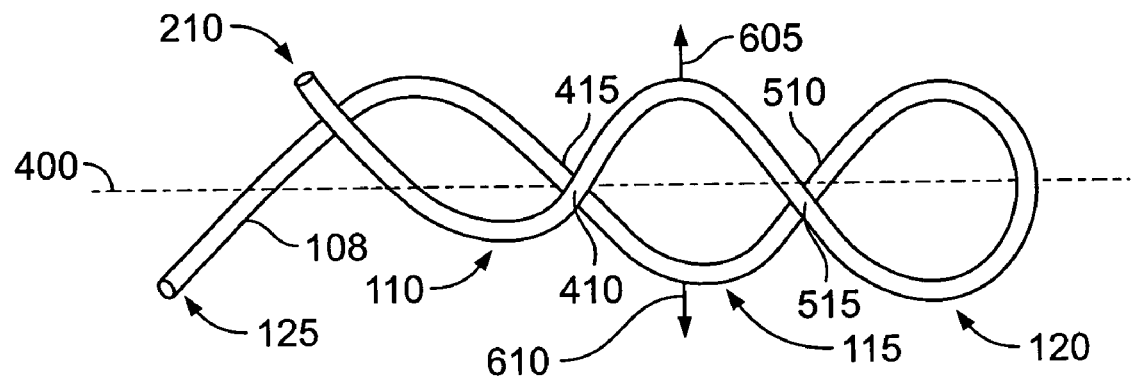
FIG. 6 is a side view of an alternative embodiment of three sub-loops formed from the adjustable loop of FIG. 2 to produce the fixation device.

Rotating adjustable loop 205, or a portion thereof, is one way to generate sub-loops 110, 115, and 120. There are, however, other processes to generate sub-loops 110, 115, and 120. FIG. 6 illustrates one of those alternative processes to generate sub-loops 110, 115, and 120. As illustrated in FIG. 6, starting with the adjustable loop 205 of FIG. 2, one side of adjustable loop 205 is moved in the direction of arrow 605 while an opposite side of adjustable loop 205 is moved in the direction of arrow 610. The moving sides eventually overlap at portions 410, 415, 510, and 515, generating sub-loops 110, 115, and 120. In this process, unlike the rotation process illustrated in FIG. 5, fourth portion 515 of adjustable loop 205 crosses and overlaps third portion 510 of adjustable loop 205 (with respect to the illustrated viewing angle).

Figure 7A:
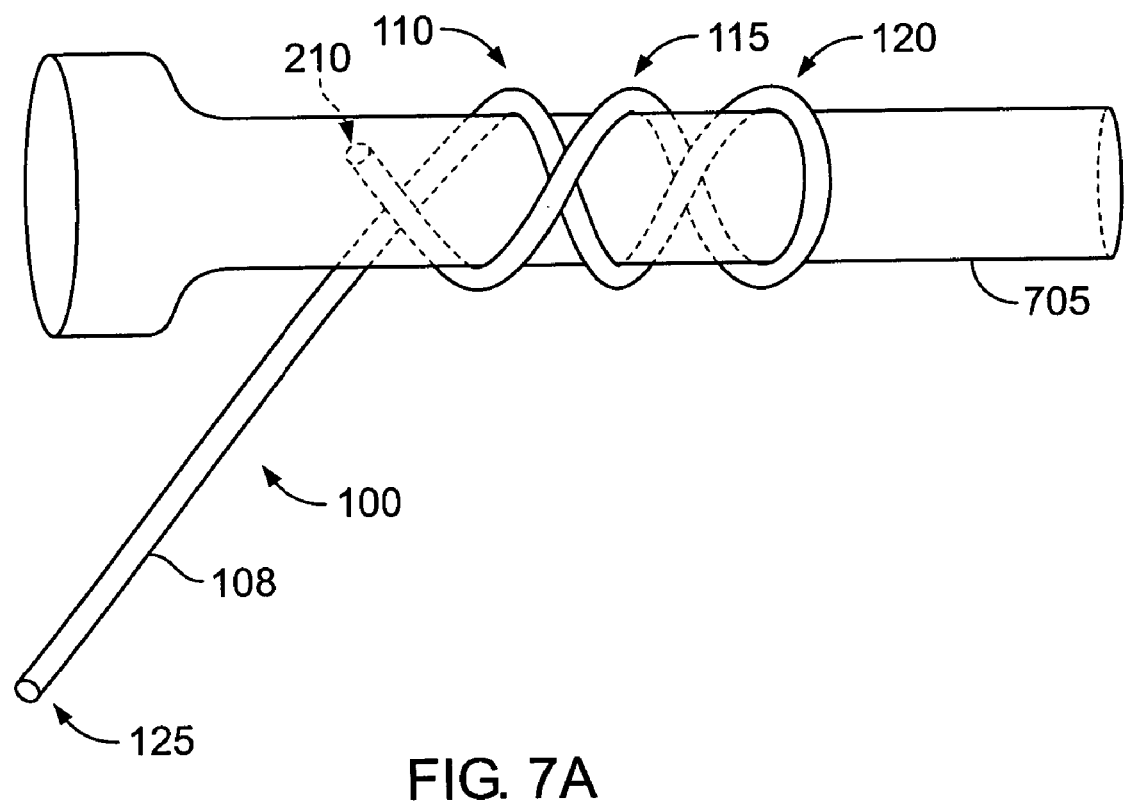
FIG. 7A is a side view of the fixation device over a cannula.
Figure 7B:
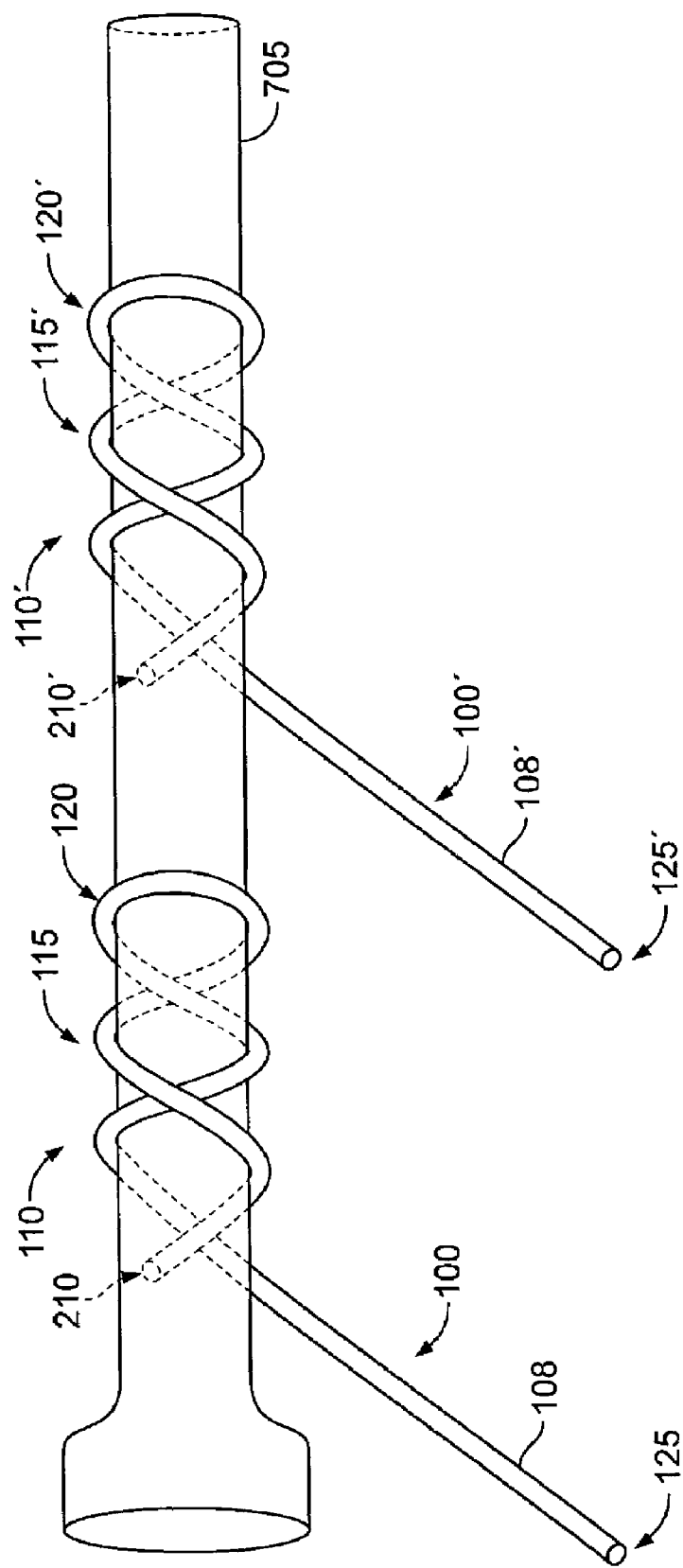
FIG. 7B is a side view of a plurality of fixation devices over a cannula.

Referring to FIG. 7A, to aid in positioning sub-loops 110, 115, and 120 around tissue 105, a device, e.g., 705 is placed through sub-loops 110, 115, and 120 along axis 400. Referring to FIG. 7B, cannula 705 can include a plurality of fixation devices 100 and 100'. In another example (not shown), cannula 705 includes four fixation devices 100.

Figure 8:
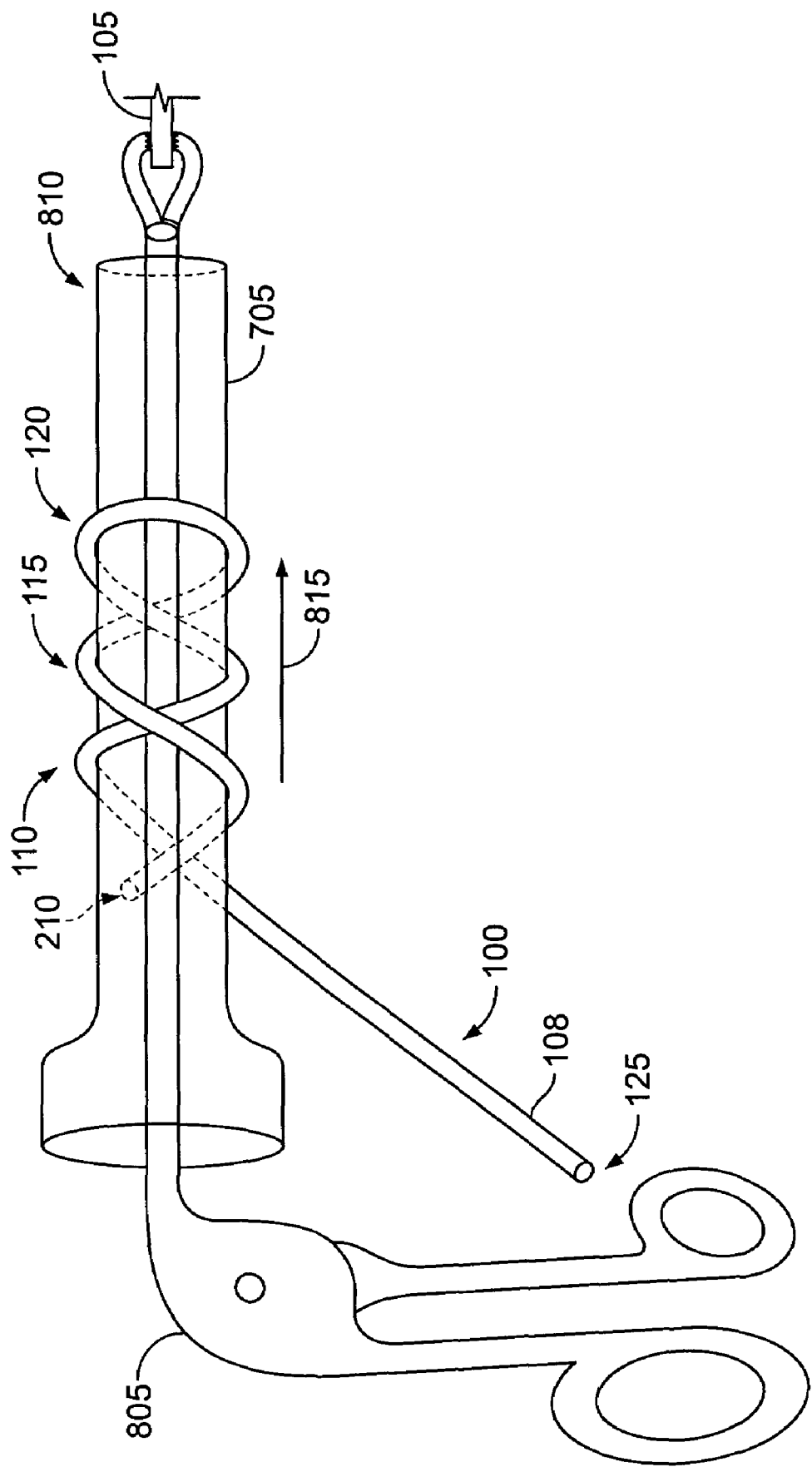
FIG. 8 is a side view of the fixation device over a cannula being used with a medical grasping device.

Referring to FIG. 8, to transfer fixation device 100 from cannula 705 onto tissue 105, a surgeon uses a grasping device 805, inserted through cannula 705, to grasp tissue 105. With tissue 105 located at an end 810 of cannula 705, the surgeon manually slides sub-loops 110, 115, and 120 in a direction indicated by arrow 815. Sub-loops 110, 115, and 120 slide off of cannula 705 and onto tissue 105. As illustrated, fixation device 100 slides off of cannula 705, onto grasping device 805 and then onto tissue 105.

In an alternative example, the surgeon can locate end 810 of cannula 705 directly over tissue 105 so that when fixation device 100 slides off of cannula 705, it falls directly onto tissue 105. In yet another alternative example, with a plurality of fixation devices 100 located on cannula 705, after attaching a first fixation device to tissue 105, the surgeon grasps another piece of tissue and slides second fixation device onto the other piece of tissue without the need to reload a fixation device between attachments.

Figure 9:
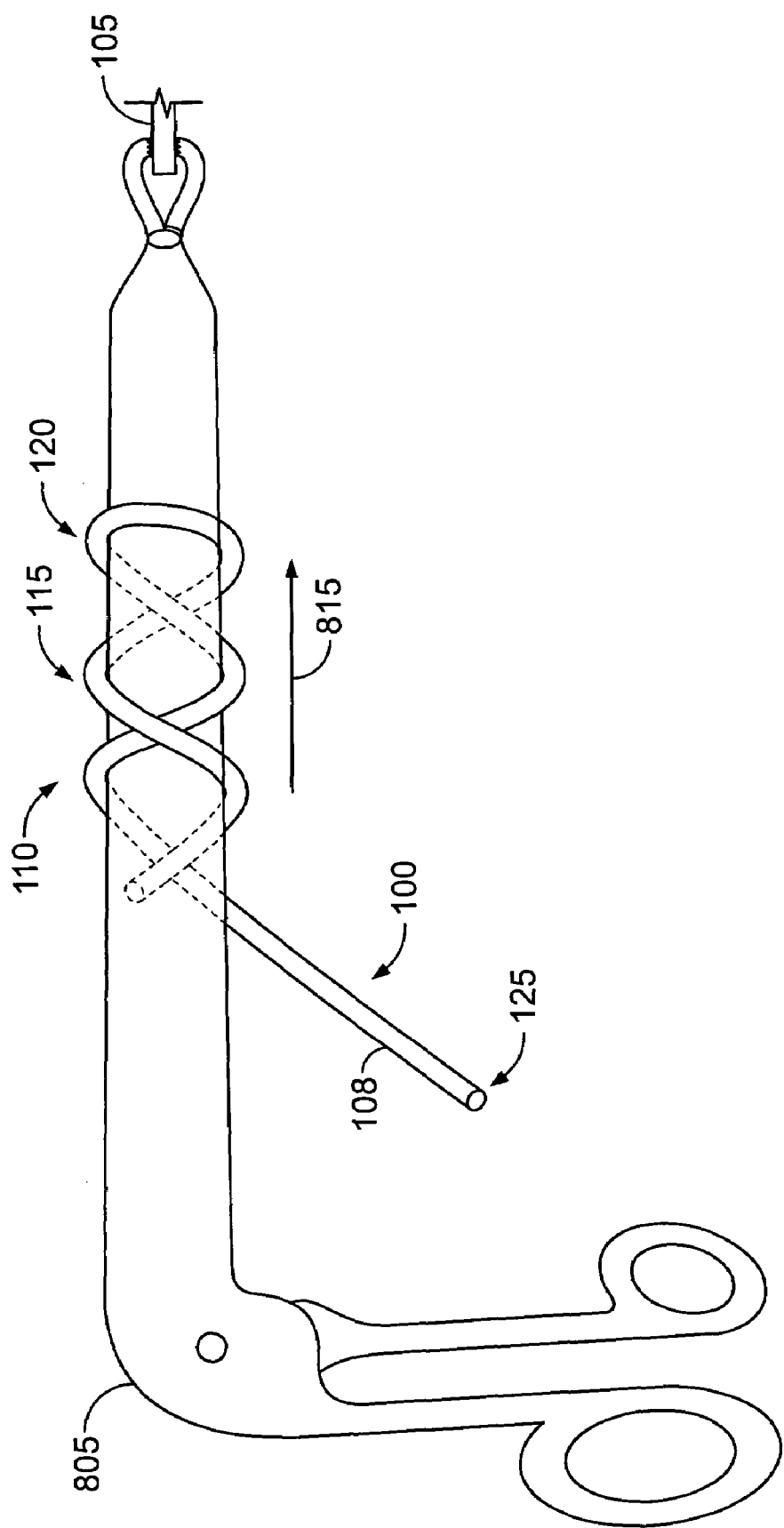
FIG. 9 is a side view of the fixation device over a medical grasping device.

Referring to FIG. 9, cannula 705 can be eliminated and the fixation device 100 located directly on the grasping device 805. Like FIG. 8, the surgeon slides sub-loops 110, 115, and 120 in a direction indicated by arrow 815. Sub-loops 110, 115, and 120 slide off of grasping device 805 and onto tissue 105.

In use, fixation device 100 allows a surgeon to easily fix suture 108 to tissue 105 so the surgeon can manipulate and direct tissue 105 as needed using suture end 125. As described above, while the surgeon pulls end 125 to direct tissue 105 during a surgical procedure, the sub-loops 110, 115, and 120 formed from adjustable loop 205 constrict and grip the tissue 105 tighter. The surgeon is able to pull and move tissue 105 to direct tissue 105, for example, through holes for receiving the tissue formed in a bone or other soft tissue. When the surgeon is done, the surgeon typically cuts off tissue portion 105a from tissue 105 and discards portion 105a.

A number of embodiments of the invention have been described. Nevertheless, it will be understood that various modifications may be made without departing from the spirit and scope of the invention. For example only and not limit the alternatives the following are some variations to the above examples. For example, other materials can be used in addition to suture for a flexible member. Also, the number of sub-loops and the process used to generate those sub-loops can vary. Also, any device can be used to help temporarily hold the fixation device so that a surgeon can locate the sub-loops onto the tissue. Also, although the term surgeon was used for clarity, any medical personnel can use the fixating device. Accordingly, other embodiments are within the scope of the following claims.

What is claimed is:

1. A medical device comprising:
    a first adjustable suture including a first sub-loop and a second sub-loop forming a figure eight configured to receive a length of tissue therethrough, each of the first sub-loop and the second sub-loop having a circumference, and the first adjustable suture having only one end configured to be pulled to decrease the circumference of the first sub-loop and the second sub-loop to fixate the first adjustable suture onto the length of tissue;
    a second adjustable suture separate from the first adjustable suture and including at least one sub-loop; and
    an assisting member disposed through the first sub-loop and through the second sub-loop of the figure eight of the first adjustable suture and disposed through the at least one sub-loop of the second adjustable suture.

2. The medical device of claim 1 wherein the assisting member comprises a medical grasping device.

3. The medical device of claim 1 wherein the assisting member comprises a cannula.

4. The medical device of claim 1 wherein the second adjustable suture includes a first sub-loop and a second sub-loop, and
    wherein the assisting member is disposed through the first sub-loop of the second adjustable suture and through the second sub-loop of the second adjustable suture.

5. The medical device of claim 1, wherein the first adjustable suture further comprises a third sub-loop configured to receive a length of tissue therethrough.

6. The medical device of claim 5 wherein the second sub-loop and the third sub-loop form a figure eight.

7. The medical device of claim 5, wherein the first adjustable suture consists of the first sub-loop, the second sub-loop, and the third sub-loop.

8. The medical device of claim 1, further comprising a plurality of adjustable sutures, each suture of the plurality of adjustable sutures including at least two sub-loops forming a figure eight through which the assisting member is disposed.

9. The medical device of claim 1,
    wherein the second adjustable suture includes a third sub-loop and a fourth sub-loop forming a second figure eight configured to receive a length of tissue therethrough,
    wherein the assisting member is disposed through the third sub-loop and through the fourth sub-loop, and
    wherein each of the third sub-loop and the fourth sub-loop has a circumference, and the second adjustable suture has only one end configured to be pulled to decrease the circumference of the third sub-loop and the fourth sub-loop.

10. A tissue fixation device comprising,
    a first suture thread having one portion of the suture thread adjustably inserted through an opening defined within another portion of the first suture thread, and including a first sub-loop and a second sub-loop forming a figure eight configured to receive a length of tissue therethrough;
    a second suture thread separate from the first suture thread and including at least one sub-loop; and
    an assisting member disposed through the first sub-loop and through the second sub-loop of the figure eight of the first suture thread and disposed through the at least one sub-loop of the second suture thread wherein the first sub-loop and the second sub-loop are configured to fixate onto tissue.

11. The tissue fixation device of claim 10 wherein the sub-loops are configured to fixate on ligament or tendon tissue.

12. The tissue fixation device of claim 10 wherein the first suture thread further comprises a third sub-loop.

13. The tissue fixation device of claim 10 wherein the suture thread is a first adjustable second suture thread includes a first sub-loop and a second sub-loop.

14. The medical device of claim 10, further comprising a plurality of adjustable sutures, each suture of the plurality of adjustable sutures including at least two sub-loops forming a figure eight through which the assisting member is disposed.

15. The medical device of claim 12, wherein the first suture thread consists of the first sub-loop, the second sub-loop, and the third sub-loop.

16. A medical device comprising:
    a first adjustable suture member, consisting of a first sub-loop, a second sub-loop, and a third sub-loop, each sub-loop configured to receive a length of tissue therethrough, the first sub-loop and the second sub-loop being joined such that, when following the first suture member along the first sub-loop and along the second sub-loop and back along the first sub-loop, the first suture member forms a first figure eight, and the first sub-loop and the third sub-loop forming a second figure eight;
    a second adjustable suture member separate from the first adjustable suture member and including at least one sub-loop; and
    a cannula disposed through the sub-loops of the figure eights of the first adjustable suture member and disposed through the at least one sub-loop of the second adjustable suture member.

17. The medical device of claim 16, further comprising a plurality of adjustable sutures, each suture of the plurality of adjustable sutures including at least two sub-loops forming a figure eight through which the cannula is disposed.

18. The medical device of claim 16,
    wherein the second adjustable suture member consists of a fourth sub-loop, a fifth sub-loop, and a sixth sub-loop, each sub-loop configured to receive a length of tissue therethrough, the fourth sub-loop and the fifth sub-loop being joined such that, when following the second suture member along the fourth sub-loop and along the fifth sub-loop and back along the fourth sub-loop, the second suture member forms a third figure eight, and the fourth sub-loop and the sixth sub-loop forming a fourth figure eight, and
    wherein the cannula is disposed through the sub-loops of the figure eights of the first adjustable suture member and the sub-loops of the figure eights of the second adjustable suture member.

19. A medical device comprising:
    a first adjustable suture thread having one portion of the first adjustable suture thread adjustably inserted through an opening defined within another portion of the first adjustable suture thread, and including a first sub-loop and a second sub-loop forming a figure eight configured to receive a length of tissue therethrough, each of the first sub-loop and the second sub-loop having a circumference, and the adjustable suture thread having only one end configured to be pulled to decrease the circumference of the first sub-loop and the second sub-loop to fixate the adjustable suture thread onto the length of tissue;

a second adjustable suture thread separate from the first adjustable suture thread and having one portion of the second adjustable suture thread adjustably inserted through an opening defined within another portion of the second adjustable suture thread, and including at least one sub-loop; and an assisting member disposed through the first sub-loop and through the second sub-loop of the figure eight of the first adjustable suture thread, and through the at least one sub-loop of the second adjustable suture thread.

20. A medical device comprising:

a first adjustable suture thread having one portion of the first adjustable suture thread adjustably inserted through an opening defined within another portion of the first adjustable suture thread, consisting of a first sub-loop, a second sub-loop, and a third sub-loop, each sub-loop configured to receive a length of tissue therethrough, the first sub-loop and the second sub-loop being joined such that, when following the first adjustable suture thread along the first sub-loop and along the second sub-loop and back along the first sub-loop, the first adjustable suture thread forms a first figure eight, and the second sub-loop and the third sub-loop forming a second figure eight;

a second adjustable suture thread separate from the first adjustable suture thread and including at least one sub-loop; and a cannula disposed through the sub-loops of the figure eights of the first adjustable suture thread and disposed through the at least one sub-loop of the second adjustable suture thread.

* * * * *